US00PP13413P2

(12) United States Plant Patent
Emery et al.

(10) Patent No.: US PP13,413 P2
(45) Date of Patent: Dec. 24, 2002

(54) HEUCHERA PLANT NAMED 'CANYON BELLE'

(76) Inventors: Dara E. Emery, deceased, late of Santa Barbara, CA (US); Michael R. Lane, legal representative, 1782 Manor Dr., Vista, CA (US) 92084; Edward L. Schneider, 1212 Mission Canyon Rd., Santa Barbara, CA (US) 93105

( * ) Notice: Subject to any disclaimer, the term of this patent is extended or adjusted under 35 U.S.C. 154(b) by 0 days.

(21) Appl. No.: 09/203,862

(22) Filed: Dec. 2, 1998

(Under 37 CFR 1.47)

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Annette Para

(57) ABSTRACT

A distinct cultivar of Heuchera plant named 'Canyon Belle', which is characterized by its compact habit, shiny dark green leaves, and rich red flowers.

2 Drawing Sheets

CROSS-REFERENCE TO RELATED APPLICATIONS

The present invention is hereby cross-referenced to the three related claimed inventions entitled Heuchera 'Canyon Duet' (Ser. No. 09/203,861), Heuchera 'Canyon Melody' (Ser. No. 09/203,863), and Heuchera 'Canyon Chimes' (Ser. No. 09/203,864) which all four together resulted from the same breeding program as herein described.

BACKGROUND TO THE INVENTION

This new cultivar of Heuchera is the result of a long-term, controlled breeding program that was conducted by Dara Emery, Plant Breeder at the Santa Barbara Botanic Garden (SBBG), from the early 1980s until his death in 1992. 'Canyon Belle' is an F2 hybrid of *Heuchera elegans* (unpatented) and a hybrid form of *Heuchera sanguinea* (unpatented). It is unascertainable which parent—*Heuchera elegans* or a hybrid form of *Heuchera sanguinea* —is the seed or pollen parent. The objective of this breeding program was to select for compact, floriferous forms of Heuchera that were more diminutive than other forms in the nursery trade. Plants that exhibited an overall dwarf stature of low-growing, mounding foliage and flowers that are similarly proportioned were selected from the various crosses made. At least one of the parents had to be a native California species, in keeping with the overall mission of SBBG's breeding program to develop garden-worthy plants from the state's native flora. In this case, *H. elegans* is the California native; it has white-pink flowers and was used for its compact size. *Heuchera sanguinea* is an Arizonan species that is much larger in habit; it was used for its red flowers.

The closest comparison plants are the parent *Heuchera elegans* and the commercial cultivar Heuchera. 'Canyon Delight' (unpatented). 'Canyon Belle' is distinguishable from *Heuchera elegans* by its larger stature, larger foliage, taller flower stalks and flower color. 'Canyon Belle' is distinguishable from Heuchera 'Canyon Delight' by its smaller foliage; glossier leaf texture and flower color.

The cultivar was first and subsequently asexually reproduced by the inventor at the Santa Barbara Botanic Garden in Santa Barbara, Calif. by vegetative cuttings. Tip cuttings 2 to 3 inches long were put in flats of medium grade perlite and placed in a lath house mist bed with bottom heat and intermittent mist of de-ionized water. All plants so obtained exhibited identical characteristics, which were true to the original plant.

A closely related cultivar is the variety Heuchera 'Canyon Delight' (unpatented), which was selected by the inventor at an earlier stage in the breeding program and introduced to commerce. It is referred to and described herein as a comparison variety but is not the subject of any claim.

SUMMARY OF THE INVENTION

The features that together distinguish this cultivar from other Heuchera cultivars are as follows:

1. Dark glossy green leaves.
2. Compact habit.
3. Rich red flowers.

BRIEF DESCRIPTION OF THE DRAWING

The accompanying photographs depict the entire plant and close-up of several flower stalks, illustrating the distinguishing overall habit and flower color, respectively. The illustrated plant is one and one half (1½ ) years old grown out of doors in open ground of loamy clay soil with morning sun and filtered afternoon shade at the Santa Barbara Botanic Garden in Santa Barbara, Calif. The color is as true as can be reasonably achieved by conventional photographic procedures.

Sheet 1 shows a young plant in a perennial border in the early stages of bloom. Note the low mounding habit.

Sheet 2 shows a close-up of several flower stalks, illustrating the rich red blossoms.

DETAILED PLANT DESCRIPTION

The following is a detailed description of the new Heuchera cultivar 'Canyon Belle'. Observations, measurements, color determinations and comparisons were made at The Santa Barbara Botanic Garden, Santa Barbara, Calif., from two-year-old plants grown out of doors in loamy clay soil with part shade. All color values are based on the 1995 Edition of The Royal Horticultural Colour Chart, Royal Horticultural Society of London, England, except where general color terms of ordinary dictionary significance are used.

Where the variety exhibits different characteristics from the comparison commercial variety Heuchera 'Canyon Delight', the relative values or dimensions are shown in parentheses. The comparison variety has been observed under the same growing and climatic conditions as the new cultivar.

Plant origin: Seedling from controlled breeding program.
Parentage: *Heuchera elegans*×*Heucherax*×*sanguinea.*
Propagation: Reproduces readily the exact same characteristics from tip cuttings or division as 'Canyon Belle'.
Rooting habit: Fibrous.
Time to develop roots: Approximately 25 days are required to form a well-developed root system.
Productivity: Produces generous number of flower stalks in spring and early summer; may rebloom again in late summer or fall with ample water.
Blooming habit: Recurrent.
Resistance to disease: We have exeprienced some losses of liners during unusally hot weather, possibly due to fungal pathogens in the soil.
Insects: As with most Heucheras, 'Canyon Belle' is susceptible to mealybug infestations.
Culture: Best in part shade and loamy soil with fairly regular watering.
Growth: Medium growth rate.
Hardiness: Estimated to be Zone 6a.
Landscape value: Small-scale groundcover, edging plant, in rock gardens, or as a container specimen.
Form: Scapose perennial with many rosettes from a semi-woody erect to ascending rootstock.
Height of plant: 35 to 45 cm ('Canyon Delight' is 40 to 55 cm tall).
Width of plant: Approx. 46 cm.
Foliage:

*Leaves: in basal rosettes.*—Petioles: Color: Close to 144A. Length: 50 to 70 mm ('Canyon Delight' leaf petioles are 50 to 120 mm long). Texture: Pilose to subhirsute. Leaf Blades (5-lobed). Length: 30 to 40 mm ('Canyon Delight' leaf blades are 35 to 50 mm long). Width: 30 to 45 mm ('Canyon Delight' leaf blades are 35 to 50 mm wide). Shape: broadly cordate to almost round. Margins: irregularly toothed, ciliate. Color: Varies between 137A and 137B. Texture: Upper surface: Glabrous. Lower surface: Gglabrous.

*Inflorescence.*—Panicle, 1 per rosette, 25 to 40 cm long. Peduncle 13 to 15 cm long; rachis puberulent. Primary branches 10 to 12, each branch with 8 to 14 flowers.

Flower ('Canyon Delight' flowers are rose-red):

*Length.*—6.5 to 8 mm long; tubular portion of hypanthium 4 to 5 mm long.

*Buds.*—Color: 50A. Length: 4 to 5 mm. Width: 2 to 3 mm. Shape: Narrowly pear-shaped.

*Hypanthium* (*Externally glandular-pubescent*).—Color: 50A. Length: 8 to 9 mm (including sepals, tube and ovary). Width: 3 mm. Shape: Narrowly campanulate. Tube length: 6 mm.

*Sepals.*—Color: 50A. Number: 5. Length: 3 mm. Width: 1.5 mm. Shape: Rounded. Texture: Glandular. Margins: Entire and glandular hairy.

*Petals.*—Color: Overall white, but faintly pink-tinged with age, color much lighter than 36D. Number: 5. Length: 4 mm inserted just below free portion of sepals. Shape: Narrowly oblanceolate. Texture: glabrous. Margins: entire and glabrous.

*Stamens.*—Number: 5. Length: 2 to 3 mm. Filaments: Color: White. Shape: Linear. Anthers: Color: 29B. Length: 1 mm. Shape: Oval.

*Pistil.*—Length: 2–3 mm. Styles: Color: White. Number: 2. Length: 1 mm. Shape: linear.

*Ovaries.*—Position: Partly inferior. Carpels (fused below midpoint to hypanthium): Color: 149B (free portions above attachment to hypanthium). Number: 2. Length: 3 mm.

*Fruit.*—Many seeded capsule. Color: 200D. Length: 6 mm. Width: 1.5 mm at base. Shape: Oblanceolate.

*Seed.*—Minute. Color: 202A. Length: 0.75 mm. Shape: Ovoid. Surface: Echinate (minutely spinose).

It is claimed:

1. A new and distinct variety of Heuchera plant named 'Canyon Belle' substantially as described and illustrated herein.

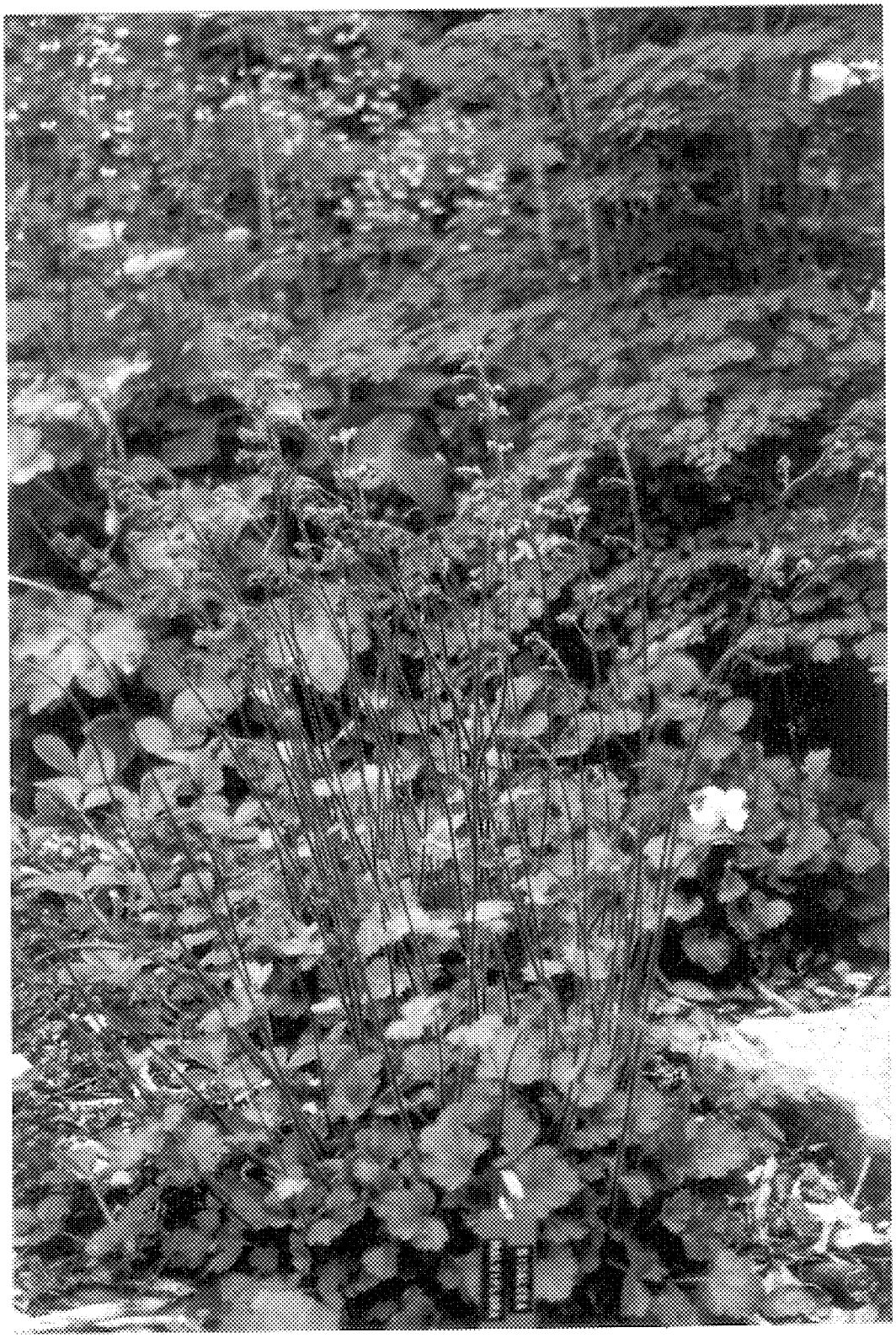

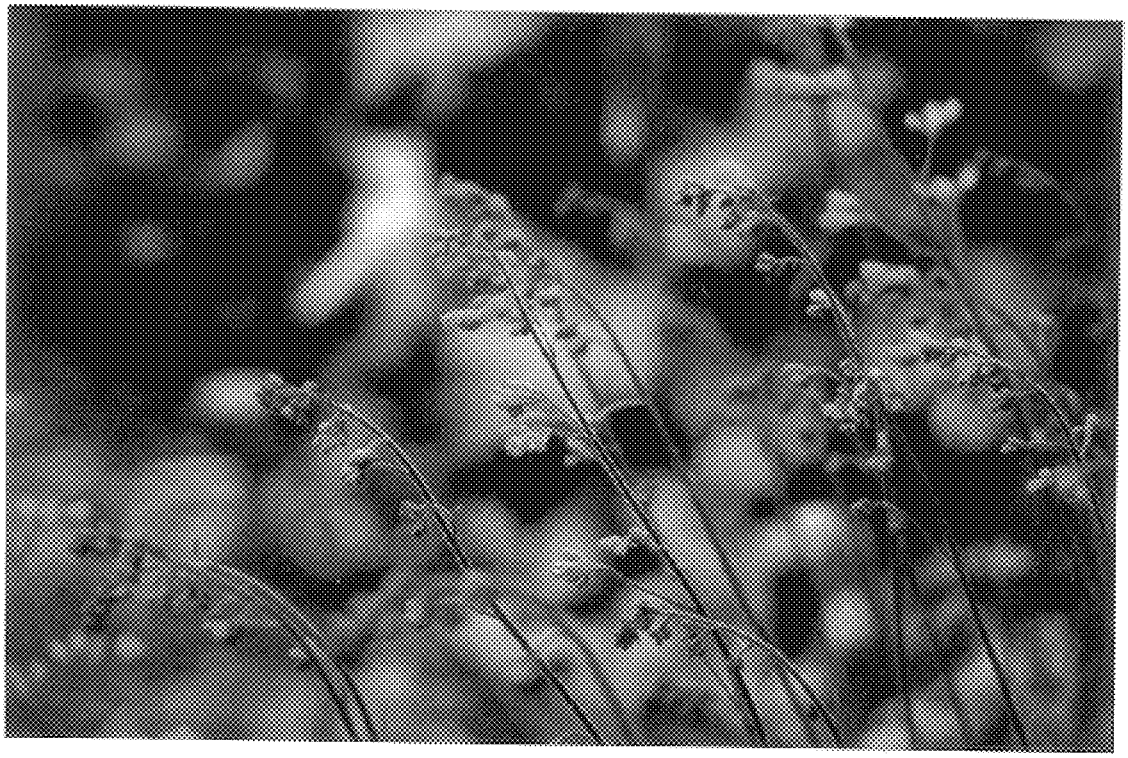

* * * * *